US008809498B2

(12) United States Patent
Borelli et al.

(10) Patent No.: US 8,809,498 B2
(45) Date of Patent: Aug. 19, 2014

(54) PEPSTATIN A DERIVATIVES

(75) Inventors: Claudia Borelli, Munich (DE); Hans Christian Korting, Berlin (DE); Elisabeth Ruge, Bad Endorf (DE); Hans Dieter Hoeltje, Berlin (DE); Robert Huber, Munich (DE); Beate Koksch, Berlin (DE); Cosimo Damiano Cadicamo, Berlin (DE)

(73) Assignee: Freie Universitaet Berlin, Berlin (DE)

( * ) Notice: Subject to any disclaimer, the term of this patent is extended or adjusted under 35 U.S.C. 154(b) by 656 days.

(21) Appl. No.: 12/990,247

(22) PCT Filed: Apr. 30, 2009

(86) PCT No.: PCT/EP2009/055301
§ 371 (c)(1),
(2), (4) Date: Dec. 1, 2010

(87) PCT Pub. No.: WO2009/133188
PCT Pub. Date: Nov. 5, 2009

(65) Prior Publication Data
US 2012/0016103 A1 Jan. 19, 2012

(30) Foreign Application Priority Data
Apr. 30, 2008 (EP) .................................... 08155527

(51) Int. Cl.
*C07K 7/06* (2006.01)
(52) U.S. Cl.
USPC .............................. 530/329; 530/330; 514/3.3
(58) Field of Classification Search
USPC .................................... 530/329, 330; 514/3.3
IPC .................................... C07K 7/06; A61K 38/55
See application file for complete search history.

(56) References Cited

U.S. PATENT DOCUMENTS

| | | | |
|---|---|---|---|
| 4,185,096 A | | 1/1980 | Castro et al. |
| 4,479,941 A | * | 10/1984 | Veber et al. ................... 514/15.8 |
| 4,481,192 A | * | 11/1984 | Cazaubon et al. ........... 514/15.6 |
| 4,716,109 A | | 12/1987 | Baker et al. |
| 4,749,687 A | | 6/1988 | Bindra et al. |

FOREIGN PATENT DOCUMENTS

| | | |
|---|---|---|
| EP | 0 081 783 A | 6/1983 |
| EP | 0 104 964 A1 | 4/1984 |
| EP | 0 117 648 A | 9/1984 |
| EP | 0 155 809 A | 9/1985 |
| EP | 0 165 151 A1 | 12/1985 |
| FR | 2531951 A | 2/1984 |
| WO | 94/00509 A | 1/1994 |
| WO | 94/24150 A2 | 10/1994 |
| WO | 96/12738 A | 5/1996 |

OTHER PUBLICATIONS

Hood S, Bonington A, Evans J, Denning D: Reduction in oropharyngeal candidiasis following introduction of protease inhibitors. AIDS 1998; 12:447-448.
Hoegl L, Korting HC, Klebe G: Inhibitors of aspartic proteases in human diseases: molecular modeling comes of age. Pharmazie 1999; 54:319-329.
Schaller M, Korting HC, Borelli C, Hube B (2005) Hydrolytic enzymes as virulence factors of *Candida albicans*. Mycoses 48: 365-377.
Ruge E, Korting HC, Borelli C (2005) Current state of three-dimensional characterization of antifungal targets and its use for molecular modelling in drug design, Int J Antimicrob. Ag. 26: 427-441.
Naglik JR, Albrecht A, Bader O, Hube B (2004) *Candida albicans* proteinases and host/pathogen interactions. Cell Microbiol 6: 915-26.
Korting HC, Hube B, Oberbauer S, Januschke E, Hamm G, Albrecht A, Borelli C, Schaller M (2003) Reduced expression of the hyphal-independent *Candida albicans* proteinase genes SAP1 and SAP3 in the efg1 mutant is associated with attenuated virulence during infection of oral epithelium, J Med Microbiol, 52: 623-632.
Hube B, Naglik K (2001) *Candida albicans* proteinases: resolving the mystery of a gene family. Microbiol 147: 1997-2005.
Abad-Zapatero C, Goldman R, Muchmore SW, Oie T, Stewart K, Cutfiled SM, Cutfield JF, Foundling SI, Ray TL (1998) Structure of secreted aspartic proteinases from *Candida*, Implications for the design of antifungal agents. Adv Exp Med Biol 436: 297-313.
Abad-Zapatero C, Goldman R, Muchmore SW, Hutchins C, Stewart K, Navaza J, Payne CD, Ray TL (1996) Structure of a secreted aspartic proteinase from *Candida albicans* complexed with a potent inhibitor: implications for the design of antifungal agents. Prot Sci 5: 640-652.
Schaller M, Korting HC, Borelli C, Hamm G, Hube B (2005) *Candida albicans* secreted aspartic proteinases (Saps) modify the epithelial cytokine response in an in vitro model of vaginal candidiasis, Infect Immun., 73(5): 2758-2765 (IF: 4,033).
Luque Irene et al, Structure-Based Thermodynamic Design of Peptide Ligands: Application to Peptide Inhibitors of the Aspartic Protease Endothiapepsin, Proteins: Structure, Function and Genetics, Alan R. Liss, US, vol. 30, No. 1, Jan. 1, 1998, pp. 74-85.
Pichova Iva et al, Secreted Aspartic Proteases of *Candida albicans, Candida tropicalis, Candida parapsilosis* and *Candida lusitaniae*: Inhibition with Peptidomimetic Inhibitors, European Journal of Biochemistry, Berlin, vol. 268, No. 9, May 1, 2001, pp. 2669-2677.
Nisato Dino et al.: Renin Inhibitors. Free-Wilson and Correlation Analysis of the Inhibitory Potency of a Series of Pepstatin Analogues on Plasma Renin; Journal of Medicinal Chemistry, US American Chemical Society, Washington, Dec. 1987, vol. 30: pp. 2287-2291.

(Continued)

*Primary Examiner* — David Lukton
(74) *Attorney, Agent, or Firm* — Maschoff Brennan

(57) ABSTRACT

The invention relates to a compound having a structure according to the general formula P3-P2-P1-P1'-P2' (I), wherein residues P3, P2, P1, P1' and P2' are specifically defined and may be, e.g., certain amino acid residues. The invention further relates to the use of said compound and to a method for synthesizing a peptide.

14 Claims, 2 Drawing Sheets

(56) References Cited

OTHER PUBLICATIONS

Omura Satoshi et al: Ahpatinins, New Acid Protease Inhibitors Containing 4-Amino-3-Hydroxy-5-Phenylpentanoic Acid; Journal of Antibiotics (Tokyo), vol. 39: pp. 1079-1085; 1986.

Guga Remy et al.: Pepstatin Analogues as Novel Renin Inhibitors; Journal of Medicinal Chemistry, American Chemical Society, Washington, US, vol. 29: pp. 1152-1159; Jul. 1986.

Hoegl L, Thoma-Greber E, Rocken M, Korting HC: HIV protease inhibitors influence the prevalence of oral candidosis in HIV-infected patients: a 2-year study. Mycoses 1998; 41:321-325.

Korting HC, Schaller M, Eder G, Hamm G, Bohmer U, Hube B: Effects of the Human Immunodeficiency Virus (HIV) Proteinase Inhibitors Saquinavir and Indinavir on In Vitro Activities of Secreted Aspartyl Proteinases of *Candida albicans* Isolates from HIV-Infected Patients. Antimicrob. Ag. Chemother. 1999; 43:2038-2042.

Cassone et al: In Vitro and In Vivo Anticandidal Activity of Human Immunodeficiency Virus Protease Inhibitors. J. Infect. Dis. 1999; 180:448-453.

Monod et al: The Inhibition of *Candida-albicans* secreted Aspartic Proteases by Three Different HIV Protease Inhibitors. Dermatology. 1999; 198(4):412-414.

Arribas JR et al: Impact of protease inhibitor therapy on HIV-related oropharyngeal candidiasis. AIDS 2000; 14:979-985.

Cauda R et al: Role of Protease Inhibitors in Preventing Recurrent Oral Candidosis in Patients With HIV Infection: A Prospective Case-Control Study. J. Acquir. Immune Defic. Syndr. 1999; 21:20-25.

Schaller M, et al: Effect of antimycotic agents on the activity of aspartyl proteinases secreted by *Candida albicans*. J. Med. Microbiol. 2003; 52:247-249.

Bein M, et al: The Secreted Aspartic Proteinases as a New Target in the Therapy of Candidiasis. Curro Drug Targets 2002; 3:351-357.

Stewart et al: *Candida* Proteases and Their Inhibition: Prospects for Antifungal Therapy. Curro Med. Chem. 2001; 8:941-948.

Cutfield et al: The crystal structure of a major secreted aspartic proteinase from *Candida albicans* in complexes with two inhibitors. Structure 1995; 3:1261-1271.

Schaller et al: Secreted aspartic proteinase (Sap) activity contributes to tissue damage in a model of human oral candidosis. Mol. Microbial. 1999; 34:169-180.

Borelli et al: The crystal structure of the secreted aspartic proteinase 3 from *Candida albicans* and its complex with pepstatin A. Proteins 2007; 68:738-748.

Borelli et al: X-ray structure of Sap 1 and Sap5: Structural comparison of the secreted aspartic proteinases from *Candida albicans*. Proteins 2008; 72: 1308-1319.

Majer et al. Structure-based specificity mapping of secreted aspartic proteases of *Candida parapsilosis, Candida albicans, and Candida tropicalis* using peptidomimetic inhibitors and homology modeling. Biol. Chern. Sep. 2006; 387 (9):1247-1254.

M. Gude, I. Ryf, P. D. White. An accurate method for the quantitation of Fmoc-derivatized solid phase supports. Letters in Peptide Science, 2002, 9, 203-206.

Naglik JR, Challacombe SJ, Hube B (2003) *Candida albicans* secreted aspartyl proteinases in virulence and pathogenesis. Microbiol Mol Bioi 67: 400-428.

J.B. Cooper: Aspartic Proteinases in Disease: A Structural Perspective; Current Drug Targets, 2002,3: 155-173.

G. Abbenante, D.P. Fairlie: Protease Inhibitors in the Clinic; Medicinal Chemistry, 2005, 1,71- 104.

Uhlikova, et al: A Modular Approach to HIV-1 Proteinase Inhibitor Design; Biochemical and Biophysical Research Communications, 1996,222: 38-43.

Pichova,et al: Development and Testing of Inhibitors of *Candida* Aspartic Proteinases; Aspartic Proteinases, 1998: 329-333.

\* cited by examiner

PEPSTATIN A DERIVATIVES

CROSS-REFERENCE TO A RELATED APPLICATION

This application is a National Phase Patent Application of International Patent Application Number PCT/EP2009/055301, filed on Apr. 30, 2009, which claims priority of European Patent Application Number 08155527.8, filed on Apr. 30, 2008.

BACKGROUND

The invention relates to a compound which is suited to act as pepstatin A analogue for the purpose of a protease inhibitor. The invention further relates to a use of such a compound, a method for synthesizing such a compound and the use of a double protected statine.

Pepstatin A is a potent inhibitor of secreted aspartic proteinases (Saps), particularly of Saps of *Candida albicans*. Saps are one of the most important virulence factors during infections of *Candida albicans* and play also important rules during infections caused by other pathogens, such as viruses, bacteria and protozoa.

Inhibiting the Saps is a powerful tool in treating Sap-related diseases. Though pepstatin A is a potent inhibitor of Saps, it cannot be used as a medicament due to its toxicity and rapid clearance in the body.

In the mid of the 90s of the 20$^{th}$ century, novel medicaments have been introduced to treat HIV (human immunodeficiency virus) infections, the so-called HIV protease inhibitors. In the context of this so-called intensified therapy it was recognized that oral candidiasis, being hitherto the most frequently occurring opportunistic infection in the course of an HIV infection, was observed much rarely in patients suffering from HIV infection (Hoegl L, Thoma-Greber E, Röcken M, Korting H C: HIV protease inhibitors influence the prevalence of oral candidosis in HIV-infected patients: a 2-year study. *Mycoses* 1998; 41:321-325).

Firstly, this reduction in occurrence of manifest oral candidiasis was thought to be based on an ameliorated immune defense due to the novel HIV therapy. Later, it was assumed that due to a structural relationship between HIV protease and Saps of *Candida albicans* also direct influences on the Saps as targets might be possible.

This assumption was experimentally tested. In 1999, it was published that HIV protease inhibitors saquinavir and indinavir influence the in vitro activity of Saps of *Candida albicans* isolates of HIV infected patients by means of inhibitory activity (Korting H C, Schaller M, Eder G, Hamm G, Böhmer U, Hube B: Effects of the human immunodeficiency virus (HIV) proteinase inhibitors saquinavir and indinavir on in vitro activities of secreted aspartyl proteinases of *Candida albicans* isolates from HIV-infected patients. *Antimicrob. Ag. Chemother.* 1999; 43:2038-2042).

Similar in vitro results were published by Cassone et al. (Cassone A, De Bernardis F, Torosantucci A, Tacconelli E, Tumbarello M, Cauda R: In vitro and in vivo anticandidal activity of human immunodeficiency virus proteins inhibitors. *J. Infect. Dis.* 1999; 180:448-453). Further, another publication was directed to the use of HIV-1 protease inhibitors such as ritonavir, saquinavir and indinavir to inhibit Saps of *Candida albicans* (Monod M, Borg-von Zepelin M, Telenti A, Sanglard D. The inhibition of *Candida-albicans*-secreted aspartic proteases by three different HIV protease inhibitors. *Dermatology.* 1999; 198(4):412-414).

The phenomenon of reducing the occurrence of oral candidiasis after introducing protease inhibitors was also described by Hood et al. with respect to observations of a single patient (Hood S, Bonington A, Evans J, Denning D: Reduction in oropharyngeal candidiasis following introduction of protease inhibitors. *AIDS* 1998; 12:447-448).

In 2000, a study was published according to which the influence of HIV protease inhibitor therapy on HIV-associated oropharyngeal candidiasis was confirmed, although is was explained by an amelioration of immune defense (Arribas J R, Hernández-Albujar S, González-Garcia J J, Peña J M, Gonzalez A, Cañedo T, Madero R, Vazquez J J, Powderly W G: Impact of protease inhibitor therapy on HIV-related oropharyngeal candidiasis. *AIDS* 2000; 14:979-985).

But as early as in 1999, it was shown in the context of a case control study that influencing the reoccurring oral candidiasis by HIV protease inhibitors cannot be explained only with an amelioration of immune defense (Cauda R, Tacconelli E, Tumbarello M, Morace G, De Bernardis F, Torosantucci A, Cassone A: Role of protease inhibitors in preventing recurrent oral candidosis in patients with HIV infection: a prospective case-control study. *J. Acquir. Immune Defic. Syndr.* 1999; 21:20-25).

In the following, it was shown that fungicides like fluconazole, which are usually used to treat oral candidiasis in the context of an HIV infection, do not significantly influence Saps of *Candida albicans*. A positive result could only be shown for the topic fungicide ciclopiroxolamin which is not used within the oral cavity (Schaller M, Krnjaic N, Niewerth M, Hamm G, Hube B, Korting H C: Effect of antimycotic agents on the activity of aspartyl proteinases secreted by *Candida albicans*. *J. Med. Microbiol.* 2003; 52:247-249).

In 2002, a publication dealt with Saps as being a novel pharmaceutical target for treatment of candidiasis (Bein M, Schaller M, Korting H C: The secreted aspartic proteinases as a new target in the therapy of candidiasis. *Curr. Drug Targets* 2002; 3:351-357). Also, works of Abad-Zapatero done in the company Abbot (USA) have been found very interesting (Stewart K, Abad-Zapatero C: *Candida* proteases and their inhibition: prospects for antifungal therapy. *Curr. Med. Chem.* 2001; 8:941-948).

Already prior to this, the crystal structure of isoenzyme 2 of Saps was solved (Cutfield S M, Dodson E J, Anderson B F, Moody P C, Marshall C J, Sullivan P A, Cutfield J F: The crystal structure of a major secreted aspartic proteinase from *Candida albicans* in complexes with two inhibitors. *Structure* 1995; 3:1261-1271).

Amongst others, Schaller et al. worked on the pathogenic relevance of Saps as main virulence factors of *Candida albicans* (Schaller M, Korting H C, Schäfer W, Bastert J, Chen W, Hube B: Secreted aspartic proteinase (Sap) activity contributes to tissue damage in a model of human oral candidosis. *Mol. Microbiol.* 1999; 34:169-180).

Structural aspects of the targets have also been considered, in particular by means of molecular modelling (Hoegl L, Korting H C, Klebe G: Inhibitors of aspartic proteases in human diseases: molecular modeling comes of age. *Pharmazie* 1999; 54:319-329).

Further, the three-dimensional structure of other Sap isoenzymes has been solved, namley that of Sap3 (Borelli C, Ruge E, Schaller M, Monod M, Korting H C, Huber R, Maskos K: The crystal structure of the secreted aspartic proteinase 3 from *Candida albicans* and its complex with pepstatin A. *Proteins* 2007; 68:738-748) as well as that of Sap1 and of Sap5 (Borelli C, Ruge E, Lee J H, Schaller M, Vogelsang A, Monod M, Korting H C, Huber R, Maskos K: X-ray structure of Sap1 and Sap5: Structural comparison of the secreted aspartic proteinases from *Candida albicans*. *Proteins* 2008; 72:1308-1319).

Various pepstatin A derivatives have been described which are effective against at least some of Saps of *Candida* species in lower concentration than that needed in case of Sap inhibition by HIV-1 protease inhibitors (Pichová I, Pavlicková L, Dostál J, Dolejsí E, Hrusková-Heidingsfeldová O, Weber J, Ruml T, Soucek M. Secreted aspartic proteases of *Candida albicans*, *Candida tropicalis*, *Candida parapsilosis* and *Candida lusitaniae*. Inhibition with peptidomimetic inhibitors. *Eur. J. Biochem.* 2001; 268(9):2669-2677; Majer F, Pavlicková L, Majer P, Hradilek M, Dolejsí E, Hrusková-Heidingsfeldová O, Pichová I. Structure-based specificity mapping of secreted aspartic proteases of *Candida parapsilosis*, *Candida albicans*, and *Candida tropicalis* using peptidomimetic inhibitors and homology modeling. *Biol. Chem.* 2006 September; 387(9):1247-1254.).

WO 94/24150 A2 and WO 96/12738 A2 describe further pepstatin A derivatives or analogues to be used as Sap inhibitors, though data concerning the efficacy of those pepstatin derivatives are not disclosed.

JP 54-163826 A describes two pepstatin A derivatives to be used as antihypertensives.

SUMMARY

It is an object of the invention to provide further pepstatin A derivatives which are suited as Sap inhibitors.

This object is achieved by a compound having a structure according to the general formula (I)

$$P3-P2-P1-P1'-P2' \quad (I),$$

wherein

P3 is W, X, Y or Z, with
  W being an amino acid derived residue having the structure $R^1$—NH—$CHR^2$—CO— with
    $R^1$ being H or a first protecting group and
    $R^2$ being the same side chain as in phenylalanine or a derivative thereof, whereby the derivative comprises phenylalanine substituted by a halogen, preferably F, Cl, Br, a linear or branched $C_1$-$C_{50}$-alkyl, $C_3$-$C_{50}$-cycloalkyl, —OH, —SH, —NH, —O—$C_1$-$C_{50}$-alkyl, —S—$C_1$-$C_{50}$-alkyl, or —N—$C_1$-$C_{50}$-alkyl,
  X being an amino acid derived residue having the structure $R^1$—NH—$CHR^3$—CO— with
    $R^1$ being H or a first protecting group and
    $R^3$ being the same side chain as in valine,
  Y being a residue having the structure —$CHR^4$— with
    $R^4$ being a linear or branched $C_3$-$C_{50}$-alkyl, a $C_3$-$C_{50}$-cycloalkyl or a $C_3$-$C_{50}$-aryl, wherein the cycloalkyl and/or aryl may be substituted by a linear or branched $C_3$-$C_{20}$-alkyl and/or an halogen, preferably F, Cl, Br, and wherein said alkyl, cycloalkyl or aryl can be interrupted or terminated by one or more substituted or non-substituted oxygen atoms, sulphur atoms and/or nitrogen atoms,
  Z being a residue having the structure $R^5$—$CHR^6$—$R^7$— with
    $R^5$ being absent or $R^1$—NH and $R^1$ being H or a first protecting group,
    $R^6$ being
      a linear or branched $C_3$-$C_{50}$-alkyl, a $C_3$-$C_{50}$-cycloalkyl or a $C_3$-$C_{50}$-aryl, wherein the cycloalkyl and/or aryl may be substituted by a linear or branched $C_3$-$C_{20}$-alkyl and/or an halogen, preferably F, Cl, Br, and wherein said alkyl, cycloalkyl or aryl can be interrupted or terminated by one or more substituted or non-substituted oxygen atoms, sulphur atoms and/or nitrogen atoms, or
    any side chain as in an amino acid,
    $R^7$ being absent or CO,
P2 is A, B or D, with
  A being a residue of an amino acid selected from the group comprising hydrophobic amino acids, charged amino acids, polar amino acids and amino acids having both a hydrophobic part and a polar or charged part, wherein the amino acid side chains may be substituted by a linear or branched $C_3$-$C_{20}$-alkyl and/or an halogen, preferably F, Cl, Br,
  B being a residue of norleucine,
  D being a residue of valine,
P1 is a residue of statine connected to P2 by a peptide bond,
P1' is a residue having the structure $R^8$—$CHR^9$—$R^7$— with
  $R^8$ being absent or NH,
  $R^9$ being
    a linear or branched $C_1$-$C_{10}$-alkyl, a $C_3$-$C_{20}$-cycloalkyl or a $C_3$-$C_{20}$-aryl, wherein the cycloalkyl and/or aryl may be substituted by a linear or branched $C_1$-$C_{10}$-alkyl and wherein said alkyl, cycloalkyl or aryl can be interrupted or terminated by one or more substituted or nonsubstituted oxygen atoms, sulphur atoms and/or nitrogen atoms, resulting in $R^9$ being nonpolar or positively charged, or
    the same side chain as in an amino acid selected from the group comprising nonpolar amino acids and positively charged amino acids,
  $R^7$ being absent or CO and
P2' is a residue of statine, wherein its carboxyl group may be protected by a second protecting group, under the provision that
  P3 can only be W if P2 is D,
  P3 can only be Z if P1' is not an alanine residue,
  P3 can only be X if P2 is B and
  P2 can only be A if P1' is not an alanine residue.

It was found that compounds as defined above show a very good efficacy against Saps of *Candida* in a much lower concentration than HIV-1 protease inhibitors used hitherto. Further, due to structural differences to pepstatin A and pepstatin A derivatives known from prior art (particularly with respect to P3 or P2 or P1'), the novel compounds show advantageous properties, e.g. with respect to toxicity and biodegradability.

E. g., it turned out that P1', which was exclusively known as alanine from prior art, can be replaced by other nonpolar or positively charged amino acids or even other nonpolar or positively charged non-amino-acid residues as defined above.

But even in case of P1' being an alanine residue, a pepstatin A derivative having a phenylalanine residue as P3 and a valine residue as P2 showed remarkable properties with respect to Sap inhibition.

Further, a pepstatin A derivative having an alanine residue as P1', a valine residue as P3 and a norleucine residue as P2 showed also very good Sap inhibition.

It should be pointed out that the development of Sap inhibitors as antifungal pharmaceuticals is based on a change of paradigm. The inhibition of virulence factors has now come to replace an influence on the structure of the pathogen or its cell wall. This might lead to a generally lower problem of newly occurring resistances. By the new methods, the fungus (which often colonizes the host without any damages for decades) is hindered to change from a harmless spherical "yeast" form into a pathogenic pseudo mycelium form and thus to get more virulent.

In the context of this invention, the terms "amino acid" or "amino acid residue" refer to any natural amino acid or amino acid residue, either proteinogenic or non proteinogenic.

The term "hydrophobic" is to be understood such that the hydrophobicity of a hydrophobic residue or side chain is comparable to or higher than that of valine.

The term "nonpolar" is to be understood such that the polarity of a nonpolar residue or side chain is comparable to or lower than that of alanine (Ala), glycine (Gly), isoleucine (Ile), leucine (Leu), methionine (Met), phenylalanine (Phe), proline (Pro), tryptophan (Trp) or valine (Val).

The term "polar" is to be understood such that the polarity of a polar residue or side chain is comparable to or higher than that of arginine (Arg), asparagine (Asn), aspartic acid (Asp), cysteine (Cys), glutamatic acid (Glu), glutamine (Gln), histidine (His), lysine (Lys), serine (Ser), threonine (Thr) or tyrosine (Tyr).

The term "positively charged" is to be understood that a positively charged residue or side chain carries at least one resulting positive charge under physiological conditions. The term "negatively charged" is to be understood accordingly with respect to negative charges. The term "charged amino acids" encompasses both negatively charged amino acids and positively charged amino acids.

If all residues P3, P2, P1, P1', P2' of structure (I) are amino acid residues, every hyphen in structure (I) represents a covalent bond being part of a peptide bond between the adjacent residues. Otherwise, a hyphen is a covalent bond between the adjacent residues, but is not necessarily part of a peptide bond.

It turned out that amino acid residues having a hydrophobic part (such as the hydrocarbon side chain of lysine) and a polar or charged part (such as the terminal side chain amino group of lysine which is positively charged under physiological conditions) are particularly well suited as P2. With pepstatin A derivatives carrying such amino acid residues as P2, a particularly high specificity between different isoenzymes of the Sap family can be achieved. Further, a high solubility of such pepstatin A derivatives is observed.

In an alternative embodiment, the side chain of $R^6$ is the same side chain as in valine, leucine, phenylalanine, tryptophan, norleucine or isoleucine. These hydrophobic residues are particularly well suited to allow an interaction of an according pepstatin A derivative with a Sap. Alternatively, $R^6$ is only one of the same side chains as in valine, leucine, phenylalanine, tryptophan, norleucine or isoleucine but not an alkyl, a cycloalkyl or an aryl as defined above. Said amino acids may be substituted by a linear or branched $C_3$-$C_{10}$-alkyl and/or Fluor.

In another embodiment, A is a residue of an amino acid selected from the group comprising valine, lysine, leucine and norleucine, being examples of hydrophobic or positively charged amino acids. Said amino acids may also be substituted by a linear or branched $C_3$-$C_{10}$-alkyl and/or Fluor.

As an alternative, $R^9$ is a residue of an amino acid selected from the group comprising alanine, arginine, lysine, ornithine and 2,4-diamino butanoic acid, being examples of nonpolar or positively charged amino acids. In another alternative, this group does not comprise alanine, but does comprise all of the other amino acids mentioned before.

In another embodiment, $R^9$ is a linear or branched $C_2$-$C_{10}$-alkyl, a $C_3$-$C_{20}$-cycloalkyl or a $C_3$-$C_{20}$-aryl, wherein the cycloalkyl and/or aryl may be substituted by a linear or branched $C_1$-$C_{10}$-alkyl and wherein said alkyl, cycloalkyl or aryl can be interrupted or terminated by one or more substituted or nonsubstituted oxygen atoms, sulphur atoms and/or nitrogen atoms, resulting in $R^9$ being nonpolar or positively charged, or is the same side chain as in an amino acid selected from the group comprising nonpolar amino acids and positively charged amino acids with the exception of alanine. Thus, in this embodiment P1' may be any amino acid but alanine or any non-amino-acid residue carrying at least a two carbon atoms in a side chain.

In a further embodiment, the first protecting group and/or the second protecting group are independently selected from each other from the group comprising tert-butyl, tert-butyloxycarbonyl (Boc), tert-butyldimethylsilyl (TBS), benzyl, benzyloxycarbonyl, 2-chloro-benzyloxycarbonyl, trityl, allyl, isovaleryl (Iva), 2,2,4,6,7-pentamethyldihydrobenzofuran-5-sulfonyl (Pbf) and 9-fluorenylmethoxycarbonyl (Fmoc).

The compound is preferably selected from the group comprising compounds with the following structure:

N-Iva-Z'-Val-Sta-Ala-Sta     (II),

Z' being Leu or an unsubstituted or substituted aromatic amino acid, preferably Phe, o-F-Phe, m-F-Phe, p-F-Phe, Tyr, p-Me-Phe or O-Me-Tyr.

The compound can also be selected from the group comprising compounds having the following structure:

N-Iva-Val-A'-Sta-Ala-Sta     (III),

A' being Lys or an unsubstituted or substituted hydrophobic amino acid, preferably Dfp-Gly, Leu, Tfe-Gly or Abu.

The compound can further be selected from the groups comprising compounds having the following structure:

P3-P2-Sta-E-Sta     (IV), whereby compounds having the following structure are preferred N-Iva-Val-Val-Sta-E-Sta     (V), E being a positively charged amino acid, preferably Lys, Orn, Dab, Arg.

In an alternative embodiment the compound is of the following structure:

Iva-Phe-Nle-Sta-Lys-Sta     (VI).

In this context, "N-Iva-Val" denotes a valine residue, the amino group of which is protected by an isovaleryl as protecting group. Accordingly, "N-Iva-Phe" denotes a phenylalanine residue which is N-protected by isovaleryl. Alternatively, unprotected amino acids could be used as P3. "Sta" denotes a statine residue (statine is 4-amino-3-hydroxy-6-methylheptanoic acid). "Orn" denotes an ornithine residue, "Nle" denotes a norleucine residue, and "Dab" denotes a 2,4-diamino butanoic acid residue, "o-F-Phe" denotes ortho-Fluoro-phenylalanine, "m-F-Phe" denotes meta-Fluoro-phenylalanine, "p-F-Phe" denotes para-Fluoro-phenylalanine, "p-Me-Phe" denotes para-Methyl-phenylalanine, "O-Me-Tyr" denotes O-methyl-tyrosine, "DfpGly" denotes Difluoropropyl-glycine, "TfeGly" denotes Trifluoroethyl-glycine, and "Abu" denotes 2-Aminobutyric acid. The other abbreviations are standard abbreviations for amino acids or amino acid residues and are also explained above.

The counter ions for positively charged compounds can be any anions like, e.g., trifluoroacetate or chloride.

The invention further relates to the use of a compound as explained above for the preparation of a medicament suited as fungicide or being effective against malaria, Alzheimer's disease, neoplasia, peptic ulcer, AIDS (acquired immunodeficiency syndrome) or hypertension. Such a medicament is suited for human or animal administration. Reference is made to table I on pages 9 and 10 of WO 94/24150 A1 giving an overview on most medically significant fungi that cause disease in humans.

The invention further relates to the use of a compound as explained above as fungicide or as a formulation being effective against malaria, Alzheimer's disease, neoplasia, peptic ulcer, AIDS or hypertension. Such fungicide or formulation may be used in human or animal administration (like a medicament) or, in case of use as fungicide, to treat plants which are affected by a fungal disease. Reference is made to table II on pages 11 and 12 of WO 94/24150 A1 giving an overview on agriculturally important plants and related fungal diseases.

In case of a medicament being effective against malaria, plasmepsins I and II are possible candidates being inhibited by the claimed compounds. In case of a medicament being effective against Alzheimer's disease, β-secretase is a possible candidate being inhibited by the claimed compounds. In case of a medicament being effective against neoplasia, cathepsin D is a possible candidate being inhibited by the claimed compounds. In case of a medicament being effective against peptic ulcer, pepsin is a possible candidate being inhibited by the claimed compounds. In case of a medicament being effective against AIDS, HIV proteases are possible candidates being inhibited by the claimed compounds. In case of a medicament being effective against hypertension, renin is a possible candidate being inhibited by the claimed compounds.

In an embodiment, the fungicide is intended to act against at least one Sap of *Candida albicans* and thus to cure or to mitigate a disease caused by *Candida albicans*.

The invention further relates to a method for synthesizing a peptide comprising a C-terminal statine, particularly a peptide having characteristics as explained above, having the following subsequent steps:

a) synthesizing a double protected statine by derivatizing the amino group of statine with a third protecting group and the side chain hydroxyl group of statine with a fourth protecting group, b) applying said double protected statine to a resin being suited for solid phase peptide synthesis (e.g. a 2-Cl-tritylchloride resin), c) allowing formation of a plurality of bonds, each between a molecule of said double protected statine and a linker being present on the resin, d) capping linkers which are not bonded to a molecule of said double protected statine, e) cleaving the third protecting group of said double protected statine, resulting in formation of single protected statine, f) applying another amino acid, the α amino group of which—or if there is no α amino group, the amino group of which—is protected with the third protecting group, to the resin, and a reactive side chain of which is protected by another protecting group, g) allowing formation of a plurality of bonds, each between a molecule of the amino acid applied in step f) and the lastly applied amino acid, h) removing amino acid molecules not bonded in step g), i) cleaving the third protecting group of the amino acid applied in step f), j) repeating steps f) to i) as often as desired and k) at least partially cleaving remaining protecting groups from the synthesized peptide and the synthesized peptide itself from the resin.

As compared to methods known from prior art, this method has the effect that the yield of a peptide synthesized by this method is significantly higher. Though it is generally possible to work with a statine, the side chain hydroxyl group of which is not protected, the efficacy of production is significantly raised due to side chain hydroxyl protection.

In an alternative embodiment, the fourth protecting group and the other protecting group are different from the third protecting group. The fourth protecting group and the other protecting group can be the same or can be different from each other. E. g., the third protecting group and/or the fourth protecting group and/or the other protecting group are independently selected from each other from the group comprising tert-butyl, tert-butyloxycarbonyl, tert-butyldimethylsilyl, benzyl, benzyloxycarbonyl, 2-chloro-benzyloxycarbonyl, trityl, allyl, isovaleryl, 2,2,4,6,7-pentamethyldihydrobenzofuran-5-sulfonyl and 9-fluorenylmethoxycarbonyl.

Using chemically different protecting groups allows cleavage of a certain protecting group of a molecule whereas another distinct protecting group remains uncleaved on the same molecule (amino acid or peptide) to be at least partially protected.

The invention also relates to the use of a statine in a solid phase peptide synthesis procedure.

In this context, the amino group of said statine is derivatized with a third protecting group and the side chain hydroxyl group of said statine is derivatized with a fourth protecting group, wherein the fourth protecting group is different from the third protecting group. The effects reached by such a modification of statine are explained above.

In an embodiment, the third protecting group and/or the fourth protecting group are independently selected from each other from the group comprising tert-butyl, tert-butyloxycarbonyl, tert-butyldimethylsilyl, benzyl, benzyloxycarbonyl, 2-chloro-benzyloxycarbonyl, trityl, allyl, isovaleryl, 2,2,4,6,7-pentamethyldihydrobenzofuran-5-sulfonyl and 9-fluorenylmethoxycarbonyl. In particular, Fmoc may be used as third protecting group and TBS may be used as fourth protecting group.

BRIEF DESCRIPTION OF THE DRAWINGS

The invention is further explained by figures and the following examples which are neither intended to limit the scope of the claimed invention nor are to be understood in such a way. In the Figures:

FIGS. 1 and 2 will be explained in detail in connection with example 5.

DETAILED DESCRIPTION

EXAMPLE 1

Figure 1:
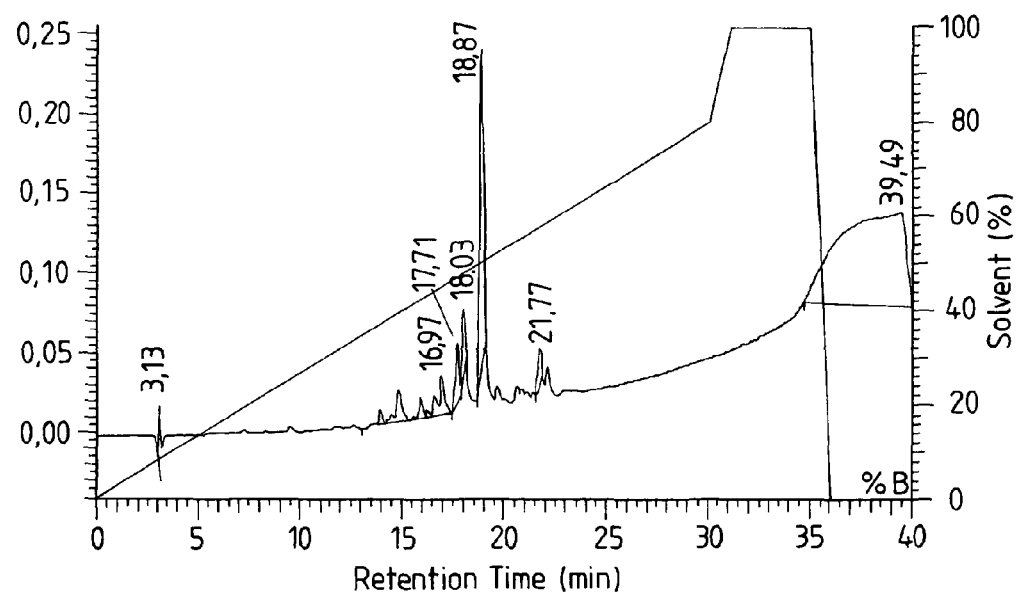
FIG. 1 shows a chromatogram of an HPLC analysis of a peptide prepared via a non-O-protected statine approach and FIG. 2 shows a chromatogram of an HPLC analysis of a peptide prepared via an O-protected statine approach.

Synthesis of (3S,4S)-3-tert-butyldimethylsilanyloxy-4-(9-fluorenylmethyloxy-carbonyl)-amino-6-methyl-heptanoic acid (N-Fmoc-O-TBS statine)

For this and the following examples the following reagents were used: All reagents of synthetic grade were used as supplied. All utilized chemicals and dimethylformamide (DMF) (Merck GmbH, D-64293 Darmstadt) for peptides synthesis were of pure analytical grade. Acetonitrile (ACN)(Acros organic, B-2440 Geel) for analytical and preparative HPLC was HPLC gradient grade. Dichloromethane (DCM) was dried over calcium hydride. Room temperature (RT) refers to 20-25° C. Air and moisture sensitive reactions were carried out under an inert atmosphere using oven-dried glassware (>100° C.). Reaction progress was monitored by thin layer chromatography (TLC) performed using Merck silica gel 60 F$_{254}$ plates. Compounds were detected by either UV or by the use of an appropriate staining agent. Column chromatography was performed using Fluka Kieselgel 60 silica gel (230-400 nm mesh).

The synthesis of N-Fmoc-O-TBS statine requires several subsequent reaction steps that are explained in the following.

Step 1: Synthesis of (2S)-5-{[1-hydroxy-4-methyl-2-(9-fluorenylmethyloxycarbonyl-amino)]-pentyl-idene}-2,2-dimethyl-1,3-dioxane-4,6-dione (3)

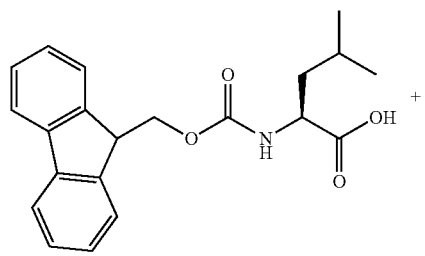

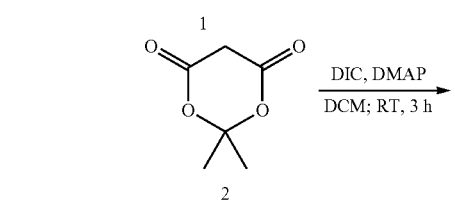

To a solution of the dried amino acid N-Fmoc-Leucine 1 (3.53 g, 10 mmol, 1 equivalent) in DCM (50 ml), Meldrum's acid 2 (1.59 g, 11 mmol, 1.1 equivalents) and 4-(dimethylamino)-pyridine (DMAP) (1.84 g, 15 mmol, 1.5 equivalents) were added. N,N-Diisopropylcarbodiimide (DIC; 1.9 ml, 12 mmol, 1.2 equivalents) was subsequently added drop-wise, and the reaction mixture was stirred at room temperature for three hours. The reaction mixture was filtered and a solution of potassium hydrogen sulfate (5 g in 50 ml H$_2$O) was added to the filtrate with vigorous stirring. After five minutes the organic phase was separated and washed first with brine and then with water. Finally the organic phase was dried over sodium sulfate and the solvent was removed under vacuum. The crude product was used for the next step without further purification.

Step 2: Synthesis of (5S)-4-Hydroxy-5-isobutyl-(9-fluorenylmethyloxycarbonyl)-pyrrol-2(5H)-one (4)

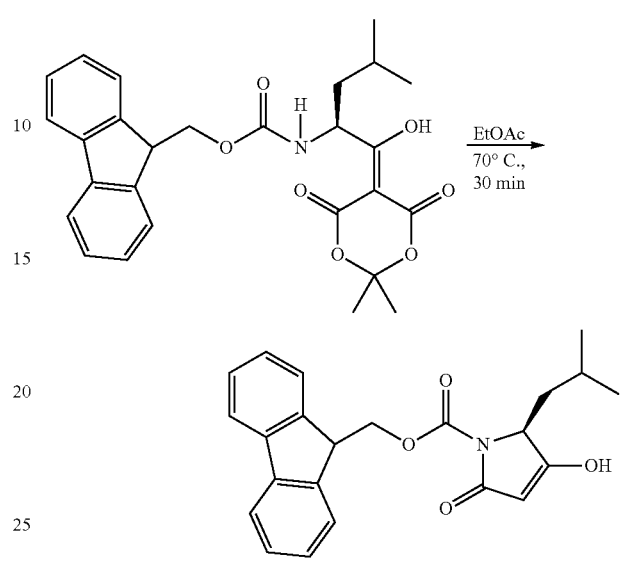

The crude product 3 was dissolved in ethyl acetate (50 ml) and the solution was heated up to 70° C. for 1 hour. Afterwards the solvent was evaporated and the product was dried under high vacuum. The crude product 4 was used for the next step without further purification.

Step 3: Synthesis of (4S,5S)-4-Hydroxy-5-isobutyl-(9-fluorenylmethyloxycarbonyl)-pyrrolidine-2-one (5)

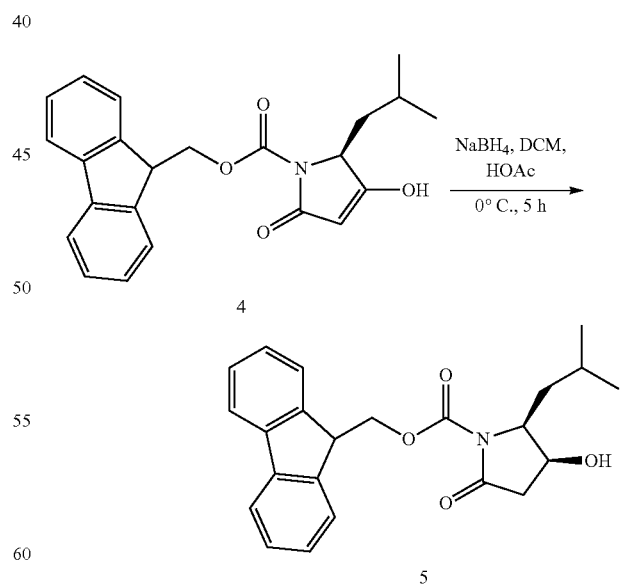

The crude product 4 was dissolved in a mixture of DCM and acetic acid (50:5 ml) and cooled to 0° C. in an ice bath. Sodium borohydride (0.7 g/10 mmol) was then added over a period of 30 minutes.

After stirring for five hours at 0° C. the mixture was first washed with brine and then with water. The organic phase was dried over sodium sulfate and the solvent was removed under vacuum.

Purification of the crude product over silica gel using a mixture of hexane/ethyl acetate as the eluent (50:50) afforded 5 as a white foam (1.52 g, 40.1%).

This and the following products were characterized by mass spectrometry. Either electron spray ionisation (ESI) time of flight (TOF) mass spectrometry or electron impact mass spectrometry (EI-MS) was applied. ESI-TOF mass spectrometry was carried out on an Agilent 6210 ESI-TOF, Agilent Technologies, Santa Clara, Calif., USA. EI-MS mass spectrometry measurements were carried out on a Varian MAT CH7-A.

Product 5 showed a mass per charge ratio of m/z (EI+) 379.1 [M+H]$^+$.

Product 5 and the following products were also characterized by nuclear magnetic resonance (NMR) spectroscopy.

All NMR spectra were measured using a Bruker AC 250 spectrometer operating at 250 MHz for $^1$H and 63 MHz for $^{13}$C, and a JEOL ECP 500 operating at 500 MHz for $^1$H and 125 MHz for $^{13}$C. All chemical shifts (δ) are reported in parts per million (ppm) and are quoted relative to the residual proton peak of CDCl$_3$ or d$_6$-DMSO (d$_6$-dimethyl sulfoxide). Spectral coupling patterns are designated as follows; d: doublet; dd: doublet of doublets; ddd: doublet of doublet of doublets; t: triplet; q: quartet; m: multiplet and br: broad signal.

δ$_H$ ppm (500 MHz; CDCl$_3$) 0.89 (6 H, dd, (CH$_3$)$_2$—CH), 1.44-1.50 (1 H, m, (CH$_3$)$_2$—CH—CH—H), 1.67-1.80 (2 H, m, (CH$_3$)$_2$—CH, (CH$_3$)$_2$—CH—CH—H), 2.36 (1 H, brs, OH), 2.64 (1 H, dd, 3-CH—H), 2.74 (1 H, dd, 3-CH—H), 4.16-4.21 (1 H, m, 5-CH), 4.30 (1 H, t, fluorenyl CH—CH$_2$O), 4.49-4.59 (3 H, m, 4-CH, fluorenyl CH—CH$_2$O), 7.33 and 7.41 (4 H, 2 pseudo t, 4×fluorenyl CH), 7.71-7.78 (4 H, m, 4×fluorenyl CH).

δ$_C$ ppm (63 MHz; CDCl$_3$) 21.9, 23.0 (CH$_3$)$_2$—CH), 24.8 (CH$_3$)$_2$—CH), 36.6 (CH$_2$CH(CH$_3$)$_2$), 40.2 (CH$_2$—CO—N), 46.5 (fluorenyl CH—CH$_2$), 60.0 (CH$_3$)$_2$—CH—CH$_2$—CH), 65.2 (CH—OH), 68.3 (fluorenyl CH—CH$_2$O), 119.8, 125.0, 127.1, 127.7 (8×fluorenyl CH), 141.1, 143.2 (4×fluorenyl quaternary C), 151.6 (N—CO—O), 171.8 (COOH).

Step 4: Synthesis of N-Fmoc-statine (6)

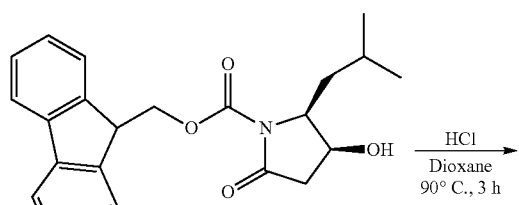

5

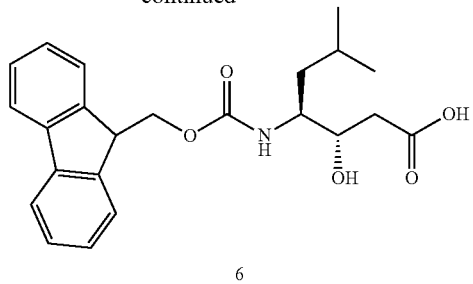

6

To a solution of 5 (1.20 g, 3.16 mmol, 1 equivalent) in dioxane (15 ml) HCl (3.00 ml, 3.16 mmol, 1 equivalent) was added and the mixture was heated to reflux for three hours. The mixture was then cooled down to room temperature and the solvent was evaporated. Ethyl acetate (50 ml) and brine (30 ml) were added and after separation the organic phase was washed with brine again. The organic phase was dried over sodium sulfate and the solvent was removed under vacuum.

Purification of the crude product over silica gel using a mixture of ethyl acetate/hexane (80:20) and 0.3% acetic acid as the eluent afforded an oil, which yielded 6 as a white solid after precipitation from an ethyl acetate/hexane solution (1.00 g, 80%).

Characterization of 6 yielded the following results:

m/z (EI+) 398.2 [M+H]$^+$

δ$_H$ ppm (500 MHz; DMSO-d$_6$) 0.85 (6 H, dd, (CH$_3$)$_2$—CH), 1.21-1.39 (2 H, m, (CH$_3$)$_2$CH—CH$_2$), 1.50-1.61 (1 H, m, (CH$_3$)$_2$—CH), 2.15 (1 H, dd, HCH—COOH), 2.37 (1H, dd, HCH—COOH), 3.54-3.61 (1 H, m, (CH$_3$)$_2$CHCH$_2$—CH), 3.84-3.91 (1 H, m, CH—OH), 4.21 (1 H, t, fluorenyl CH—CH$_2$O), 4.25-4.35 (2 H, m, fluorenyl CH—CH$_2$O), 6.94 (1 H, d, NH), 7.31 (2 H, dd, 2×fluorenyl CH), 7.41 (2 H, pseudo t, 2×fluorenyl CH), 7.71 (2 H, pseudo t, 2×fluorenyl CH), 7.88 (2 H, d, 2×fluorenyl CH).

δ$_C$ ppm (63 MHz; DMSO-d$_6$) 21.7, 23.3 (CH$_3$)$_2$—CH), 24.3 (CH$_3$)$_2$—CH), 38.2 (CH$_2$—COOH), 38.6 (CH$_3$)$_2$CH—CH$_2$), 46.8 (fluorenyl CH—CH$_2$O), 52.6 (CH$_3$)$_2$CHCH$_2$—CH), 65.0 (fluorenyl CH—CH$_2$O), 69.1 (CH—OH), 120.0, 125.1, 126.9, 127.5 (8×fluorenyl CH), 140.1, 143.7, 142.8 (4×fluorenyl quaternary C), 156.0 (N—CO—O), 173.0 (COOH).

The NMR analysis showed that 6 exists as an equilibrium mixture of isomers in a ratio of ~9:1, probably due to the carbamate E/Z isomerization. However, we report only the NMR data for the major isomer.

Step 5: Synthesis of N-Fmoc-O-TBS-statine (7)

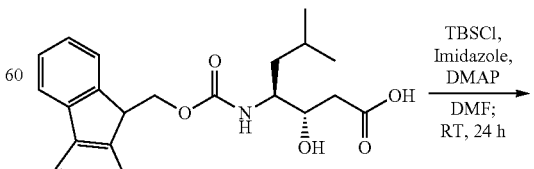

6

-continued

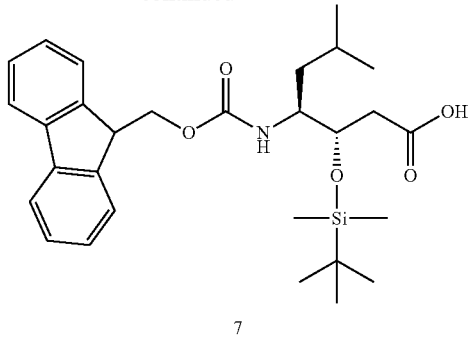

7

The product 6 (1.02 g, 2.57 mmol, 1 equivalent) was dissolved in DMF (4.00 ml) under inert atmosphere. After adding imidazole (1.02 g, 14.98 mmol, 6 equivalents), tert-butyldimethylchloride (TBSCl, 1.14 g, 7.56 mmol, 3 equivalents) and a catalytic amount of DMAP, the reaction mixture was stirred for five hours at room temperature.

Imidazole (1.02 g, 14.98 mmol, 6 equivalents) and TBSCl (1.14 g, 7.56 mmol, 3 equivalents) were then added again and the reaction was left for 24 hours under stirring. Methanol (9.70 ml/1.1 mmol) was then added and the mixture was stirred for another hour. This mixture was diluted with 25% citric acid (20 ml) and extracted with ethyl acetate (3×20 ml). The combined extracts were washed with water and with brine and finally dried over sodium sulfate. Evaporation of the solvent gave a viscous oil, which was purified over silica gel using a mixture of ethyl acetate/hexane (70:30) and 0.1% acetic acid as the eluent. The final product 7 was afforded as a white solid after precipitation from a cyclohexane/ether solution (1.14 g, 86%).

Characterization of 7 yielded the following results:

m/z (ESI+) 512.3 [M+H]$^+$

NMR data for the major isomer:

$\delta_H$ ppm (500 MHz; d$_6$-DMSO) 0.01 (3 H, s, Si—C$\underline{H}_3$), 0.08 (3 H, s, Si—C$\underline{H}_3$), 0.76-0.91 (15 H, m, (C$\underline{H}_3$)$_2$—CH, C(C$\underline{H}_3$)$_3$), 1.22-1.32 (2 H, m, (CH$_3$)$_2$—CH—C$\underline{H}_2$), 1.50-1.60 (1 H, m, (CH$_3$)$_2$—C$\underline{H}$), 2.10 (1H, dd, HC$\underline{H}$—COOH), 2.46 (1 H, d, $\underline{H}$CH—COOH), 3.55-3.65 (1H, m, (CH$_3$)$_2$CHCH$_2$—C$\underline{H}$), 4.02-4.11 (1 H, m, C$\underline{H}$—O—Si—(CH$_3$)$_2$), 4.21 (1H, t, fluorenyl C$\underline{H}$—CH$_2$O), 4.25-4.40 (2 H, m, fluorenyl CH—C$\underline{H}_2$O), 7.18 (1 H, d, NH), 7.32 (2 H, ddd, 2×fluorenyl CH), 7.41 (2 H, pseudo t, 2×fluorenyl CH), 7.68 (2 H, pseudo t, 2×fluorenyl CH), 7.88 (2H, d, 2×fluorenyl CH), 12.17 (1H, brs, COOH).

$\delta_C$ ppm (125 MHz; d$_6$-DMSO) −5.1, −4.8 (CH$_3$)$_2$Si), 17.5 ($\underline{C}$(CH$_3$)$_3$), 21.3, 23.5 ($\underline{C}$H$_3$)$_2$—CH), 24.3 (CH$_3$)$_2$—$\underline{C}$H), 25.6 (C($\underline{C}$H$_3$)$_3$), 35.5 (CH$_3$)$_2$—CH—$\underline{C}$H$_2$), 37.1 ($\underline{C}$H$_2$—COOH), 46.8 (fluorenyl $\underline{C}$H—CH$_2$O), 52.6 (CH$_3$)$_2$—CH—CH$_2$—$\underline{C}$H), 65.0 (fluorenyl CH—$\underline{C}$H$_2$O), 71.0 ($\underline{C}$H—OSi—(CH$_3$)$_2$), 120.0, 125.0, 126.9, 127.5 (8×fluorenyl CH), 140.6, 140.7, 143.7, 143.8 (4×fluorenyl quartenary C), 155.8 (N—CO—O), 173.1 (COOH).

Example 2

Peptide Synthesis

Different peptides were synthesized manually on a scale 0.1 mmol via a solid-phase methodology using a 2-Cl-tritylchloride resin and Fmoc-protected amino acids. All amino acids were purchased from company Gerhardt, D-34466 Wolfhagen, with exception of statine (N-Fmoc-O-TBS-statine) which was synthesized according to example 1 (see above). Amino acid side chain protection was as follows: Lys(Boc), Dab(Boc), Orn(Boc), Arg(Pbf), Sta(TBS). "Boc" denotes tert-butyloxycarbonyl, "Pbf" denotes 2,2,4,6,7-pentamethyldihydrobenzofuran-5-sulfonyl, "TBS" denotes tert-butyldimethylsilyl and "Fmoc" denotes 9-fluorenylmethoxycarbonyl.

Step 1: Preparation of the N-Fmoc-O-TBS-statine Loaded Resin

The 2-Cl-tritylchloride resin (268.5 mg, 0.775 mmol/g) was swollen in DCM (3 ml) in a syringe with a sinter for ten minutes. After the swelling, the solvent was removed. N-Fmoc-O-TBS-statine (52 mg, 0.101 mmol) and diidopropylethylamine (DIPEA, 75 µl, 0.43 mmol) were dissolved in dry DCM (4 ml) and this solution was added to the resin. The mixture was shaken for three hours.

After removing the solvent, the free 2-Cl-tritylchloride linkers were capped by treatment of the resin with a solution of DCM/methanol/DIPEA (17:2:1 (v:v:v)) (3×6 ml) for 15 minutes, and subsequently with a solution of DMF/DIPEA/acetic anhydride (8:1:1 (v:v:v)) (2×5 ml) for 20 minutes. The resin was then washed with DMF (2×3 ml) and with DCM (4×3 ml), and finally was dried under vacuum. The loading and loading efficiency were determined to be 0.36 mmol/g and 90%, respectively, using the method described by Markus Gude and co-workers (M. Gude, J. Ryf, P. D. White, *Letters in Peptide Science*, 2002, 9, 203-206.)

Step 2: Fmoc-Cleavage

Fmoc deprotection was carried out with a solution of 2% 1,8-diazabicyclo[5.4.0]undec-7-ene (DBU) and 2% piperidine in DMF (6 ml) after each coupling step. This solution was added in two batches to the resin, and the mixture was shaken after each addition for 20 minutes. Finally the resin was rinsed with DMF (6×3 ml).

Step 3: Coupling of the Amino Acids

All amino acids were coupled following preactivation to the corresponding HOAt ester using 1.3 equivalents of 1-hydroxy-7-azabenzotriazole (HOAt), and 1.2 equivalents of DIC in DMF (6 ml). This solution was added to the resin and the mixture was stirred typically for 4 hours. Each coupling was performed twice using a threefold excess of the amino acid. In the case of statine, the first coupling was carried out overnight using 1.5 equivalents of the amino acid, whereas for the second coupling the resin was stirred for 4 hours in the presence of 1 equivalent of statine. After each coupling step, the resin was rinsed with DMF (6×3 ml).

Step 4: Acylation of the N-terminal Group

The acylation of the amino terminal group was performed prior to cleavage of the resin with trifluoro acetic acid (TFA). Isovaleryl chloride (2 equivalents) was dissolved in DMF (6 ml) in the presence of DIPEA (6 equivalents). This solution was added to the resin and the mixture was shaken for 20 minutes. This operation was repeated and the resin was then washed with DMF (3×3 ml), and finally with DCM (4×3 ml).

Step 5: Cleavage of the Resin and Protecting Groups

A solution of TFA/triisopropylsilane/H$_2$O (90:8:2 (v:v:v)) (3 ml) was added to the resin and the mixture was stirred for 90 minutes. After the resin was filtered out, ice cold diethyl ether was added to the solution and the mixture was stored in the freezer. The solid formed was separated from the solution by centrifugation and dried under vacuum.

Step 6: Purification of the Peptides

The crude peptides were purified by preparative high performance liquid chromatography (HPLC). Purification was done by reversed phase HPLC on a smartline manager 5000 system (Knauer GmbH, D-14163 Berlin) equipped with two smartline pumps 1000 and a UV detector 2500 on a LUNA™ C8(2) column (10 µm particle size, 300 Å pore size, 250× 21.20 mm inner diameter, Phenomenex®, USA). Approximately 25 mg of each crude peptide were dissolved in 10 ml of 50% ACN, 50% $H_2O$ and 0.1% TFA (v/v/v) and multiply injected into the HPLC apparatus. The purification was performed under a linear A and B gradient, where solvent A was 99.9% $H_2O$ and 0.1% TFA (v/v) and solvent B was 99.9% ACN and 0.1% TFA (v/v). The applied gradient to isolate the pure peptides was a linear gradient from 95% A, 5% B to 40% A, 60% B over 30 min. The flow rate was 20 ml/min and absorbance was recorded at 230 nm.

Pooled fractions containing the peptide were collected and the solution concentrated on a rotary evaporator until complete removal of ACN and TFA. The peptides that were not soluble in water were dissolved (or partially dissolved) with acetic acid (~10%) and the solution was subsequently lyophilized. The peptides that were afforded as TFA salts, which are instead soluble in water, were lyophilized without addition of acetic acid.

Example 3

Properties of Different Synthesized Peptides

Different peptides were synthesized according to the method as explained in example 2 (see above). The peptides were characterized by mass spectrometry (see above). The following results were obtained:

Peptides Modified at the P2 Position

P2(Nle)-pepstatin ((N-Iva-Val)-N/e-Sta-Ala-Sta): 28.6 mg product were obtained after purification (~41.0% total yield after purification; 100% would correspond to the theoretical yield without any product loss); m/z (ESI+) 700.5 [M+H]$^+$ P2(Leu)-pepstatin ((N-Iva-Val)-Leu-Sta-Ala-Sta) (prior art): 28.0 mg product were obtained after purification (~40.0% total yield after purification); m/z (ESI+) 700.5 [M+H]$^+$ P2(Lys)-pepstatin ((N-Iva-Val)-Lys-Sta-Ala-Sta) (used as control): 23.2 mg product were obtained after purification (~28.0% total yield after purification); m/z (ESI+) 715.5 [M+H]$^+$ Obtained as TFA salt; MW: 828.5

P2(DfpGly)-pepstatin ((N-Iva-Val)-DfpGly-Sta-Ala-Sta): 28.1 mg product were obtained after purification (~39.0% total yield after purification); m/z (ESI+) 722.45 [M+H]$^+$ P2(TfeGly)-pepstatin ((N-Iva-Val)-TfeGly-Sta-Ala-Sta): 31.0 mg product were obtained after purification (42.7% total yield after purification); m/z (ESI+) 726.4 [M+H]$^+$ P2(Abu)-pepstatin ((N-Iva-Val)-Abu-Sta-Ala-Sta) (prior art): 27.0 mg product were obtained after purification (40.2% total yield after purification); m/z (ESI+) 672.5 [M+]$^+$ Peptides Modified at the P1' Position P1'(Lys)-pepstatin ((N-Iva-Val)-Val-Sta-Lys-Sta): 34.2 mg product were obtained after purification (~40.0% total yield after purification); m/z (ESI+) 743.5 [M+H]$^+$ Obtained as TFA salt; MW: 856.5

P1'(Orn)-pepstatin ((N-Iva-Val)-Val-Sta-Orn-Sta): 50.5 mg product were obtained after purification (~60.0% total yield after purification); m/z (ESI+) 729.5 [M+H]$^+$ Obtained as TFA salt; MW: 842.5

P1'(Dab)-pepstatin ((N-Iva-Val)-Val-Sta-Dab-Sta): 41.4 mg product were obtained after purification (~50.0% total yield after purification); m/z (ESI+) 715.5 [M+H]$^+$ Obtained as TFA salt; MW: 828.5

P1'(Arg)-pepstatin ((N-Iva-Val)-Val-Sta-Arg-Sta): 57.5 mg product were obtained after purification (~65.0% total yield after purification); m/z (ESI+) 771.5 [M+H]$^+$ Obtained as TFA salt; MW: 884.5

Peptides Modified at the P3 Position

P3(Leu)-pepstatin ((N-Iva-Leu)-Val-Sta-Ala-Sta) (prior art): 28.0 mg product were obtained after purification (~45.0% total yield after purification); m/z (ESI+) 700.5 [M+H]$^+$ P3(Phe)-pepstatin ((N-Iva-Phe)-Val-Sta-Ala-Sta): 26.2 mg product were obtained after purification (~41.0% total yield after purification); m/z (ESI+) 734.5 [M+H]$^+$ P3(p-MePhe)-pepstatin ((N-Iva-pMePhe)-Val-Sta-Ala-Sta): 45.0 mg product were obtained after purification (60.2% total yield after purification); m/z (ESI+) 748.5 [M+H]$^+$ P3(O-MeTyr)-pepstatin ((N-Iva-OMeTyr)-Val-Sta-Ala-Sta): 38.3 mg product were obtained after purification (50.1% total yield after purification); m/z (ESI+) 764.5 [M+H]$^+$ P3(Tyr)-pepstatin ((N-Iva-Tyr)-Val-Sta-Ala-Sta): 33.7 mg product were obtained after purification (~45% total yield after purification); m/z (ESI+) 750.47 [M+H]$^+$ P3(o-FPhe)-pepstatin ((N-Iva-oFPhe)-Val-Sta-Ala-Sta): 32.3 mg product were obtained after purification (~43.0% total yield after purification); m/z (ESI+) 752.5 [M+H]$^+$ P3(m-FPhe)-pepstatin ((N-Iva-mFPhe)-Val-Sta-Ala-Sta): 33.1 mg product were obtained after purification (~44.0% total yield after purification); m/z (ESI+) 752.5 [M+H]$^+$ P3(p-FPhe)-pepstatin ((N-Iva-pFPhe)-Val-Sta-Ala-Sta): 32.2 mg product were obtained after purification (42.8% total yield after purification); m/z (ESI+) 752.5 [M+H]$^+$ Peptide Modified at the P3, P2 and P1' Position Compound K ((N-Iva-Phe)-Nle-Sta-Lys-Sta): 32 mg product were obtained after purification (34.8% total yield after purification); m/z (ESI+) 805.5 [M+H]$^+$ Obtained as TFA salt; MW: 918.5

Example 4

Inhibitory Activity of Sap Inhibitors Against Saps of *Candida albicans*

To determine the inhibitory activity of different Sap inhibitors (amongst them pepstatin A and compounds according to the invention) against different Saps of *Candida albicans* the $IC_{50}$ value (representing the necessary concentration of an inhibitor to reduce the activity of an enzyme for 50%) was identified. For this purpose, that inhibitor concentration was determined in vitro at which the proteolytic activity of the enzyme or its velocity of metabolizing a substrate, respectively, was reduced for 50%.

The proteolytic activity of the tested Saps was determined at the pH optimum of those Saps. Resorufin-marked casein was used as substrate. Proteolysis of casein can be detected by an increase in fluorescence due to released resorufin (a fluorescence marker) by proteolysis.

Sap1, Sap3 and Sap6 of *Candida albicans* were independently dissolved in 2-(N-morpholino)ethanesulfonic acid (MES) having a concentration of 10 mmol/l and a pH of 6.5 resulting in enzyme solutions having a Sap concentration of 100 mmol/l. After one hour incubation at room temperature, 80 μl of a substrate solution comprising resorufin-marked casein in a sodium citrate buffer having a concentration of 500 mmol/l and a pH of 3.5 (in case of Sap3), 4.5 (in case of Sap1) and 5.0 (in case of Sap6) were added to 20 μl of enzyme solution. The resulting Sap concentration was 5 nmol/l. The resulting casein concentration was chosen such that the Saps could work in excess of substrate. Different Sap inhibitors were added, resulting in a final inhibitor concentration of 1 nmol/l, 2 nmol/l, 5 nmol/l, 10 nmol/l, nmol/l or 50 nmol/l in each case. One enzyme-substrate sample was left without addition of inhibitor. All experiments were performed in triplicate.

The mixture of enzyme and substrate or of enzyme, substrate and inhibitor was incubated at 37° C. under agitation at 300 rpm (rounds per minute) for 60 min in each case. Afterwards, 20 μl of a trichloroacetic acid solution (30%, w/v) were added. The mixture was placed on ice for 5 minutes and centrifuged afterwards for 3 min at 6000 rpm. The supernatant was removed.

To carry out fluorescence measurements, 100 μl of the supernatant were mixed with 100 μl Tris-HCl (trishydroxymethylaminomethane-HCl) having a concentration of 1 mol/l and a pH of 10.0. The fluorescence of this mixture was measured directly after adding Tris-HCl using an excitation wavelength of 530 nm and an emission wavelength of 590 nm on a CytoFluor 2350 apparatus (Millipore, Bedford, Mass., USA), wherein sensitivity was set to 2 and bandwidth was set to 7.

The average of three independent fluorescence measurements was calculated. The fluorescence of enzyme without inhibitor (i.e. inhibitor concentration of 0 nmol/l) was set to 100% enzyme activity. The activity of inhibited enzyme was calculated accordingly from the fluorescence of inhibited enzyme with respect to fluorescence of enzyme without inhibitor. Finally, the enzyme activity was plotted against the inhibitor concentration and the $IC_{50}$ value was determined.

The following table 1 shows the results for the determined $IC_{50}$ values.

TABLE 1

$IC_{50}$ values for different inhibitors on the activity of Sap1, Sap3 and Sap6 of *Candida albicans*.

| name | MW | IC50 Sap1 | Sap3 | Sap5 | Sap6 |
|---|---|---|---|---|---|
| Pepstatin A | 685.892 | ~7 nM | ~1 nM | 5 nM | ~7 nM |
| Amprenavir | 505.64 | ~5 μM | ~20 μM | ~33 μM | >50 μM |
| Ritonavir | 720.95 | ~2 μM | ~5 μM | >50 μM | ~33 μM |
| Nelfinavir | 663.9 | ~250 μM | >312 μM | | |
| Saquinavir | 766.96 | ~50 μM | ~200 μM | | >312 μM |
| Lopinavir | 628.8 | 312 μM | >312 μM | >312 μM | >312 μM |

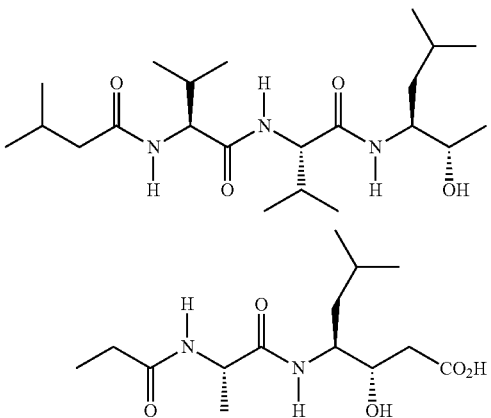

TABLE 1-continued

IC$_{50}$ values for different inhibitors on the activity of Sap1, Sap3 and Sap6 of *Candida albicans*.

| name | MW | IC50 Sap1 | Sap3 | Sap5 | Sap6 |
|---|---|---|---|---|---|
| P2(Lys)-pepstatin | 828.49 | >500 nM | ~100 nM | ~20 nM | 50 nM |
| P2(Nle)-pepstatin | 699.48 | ~10 nM | <5 nM | 10 nM | ~15 nM |

TABLE 1-continued
IC₅₀ values for different inhibitors on the activity of Sap1, Sap3 and Sap6 of *Candida albicans*.
| name | | MW | IC50 Sap1 | Sap3 | Sap5 | Sap6 |
|---|---|---|---|---|---|---|
| 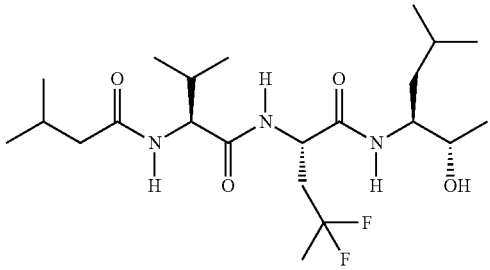 | P2(DfpGly)-pepstatin | 721.45 | ~20 nM | ~5 nM | | ~15 nM |
| 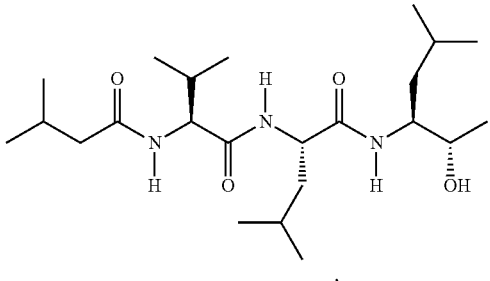 | P2(Leu)-pepstatin | 699.48 | >500 nM | 100 nM | | ~200 nM |
| 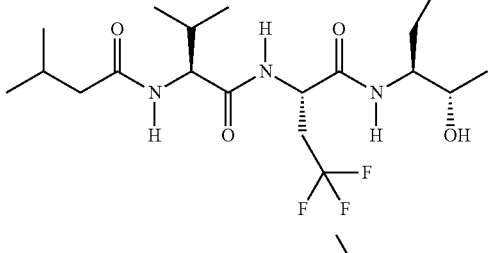 | P2(TfeGly)-pepstatin | 725.4 | ~50 nM | <5 nM | | ~20 nM |

TABLE 1-continued

IC₅₀ values for different inhibitors on the activity of Sap1, Sap3 and Sap6 of *Candida albicans*.

| name | MW | IC50 Sap1 | Sap3 | Sap5 | Sap6 |
|---|---|---|---|---|---|
| P2(Abu)-pepstatin | 671.5 | ~50 nM | <5 nM | | ~20 nM |
| P1'(Lys)-pepstatin | 856.51 | <5 nM | <5 nM | | ~7 nM |
| P1'(Orn)-pepstatin | 842.5 | ~20 nM | ~15 nM | | ~30 nM |

TABLE 1-continued

IC$_{50}$ values for different inhibitors on the activity of Sap1, Sap3 and Sap6 of *Candida albicans*.

| name | MW | IC50 Sap1 | Sap3 | Sap5 | Sap6 |
|---|---|---|---|---|---|
| P1'(Dab)-pepstatin | 828.48 | ~400 nM | ~20 nM | | >500 nM |

G

| | | | | | |
|---|---|---|---|---|---|
| P1'(Arg)-pepstatin | 884.52 | ~10 nM | <5 nM | | <5 nM |

H

TABLE 1-continued
IC$_{50}$ values for different inhibitors on the activity of Sap1, Sap3 and Sap6 of *Candida albicans*.
| name | MW | IC50 Sap1 | Sap3 | Sap5 | Sap6 |
|---|---|---|---|---|---|
| 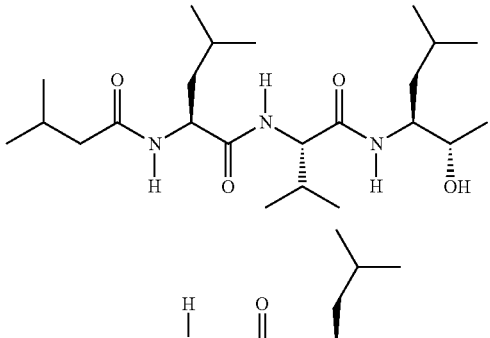 P3(Leu)-pepstatin | 699.48 | >500 nM | <5 nM | | >500 nM |
| 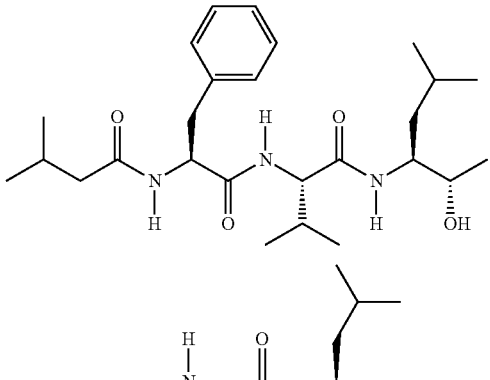 P3(Phe)-pepstatin | 733.46 | ~5 nM | <5 nM | | ~10 nM |
| 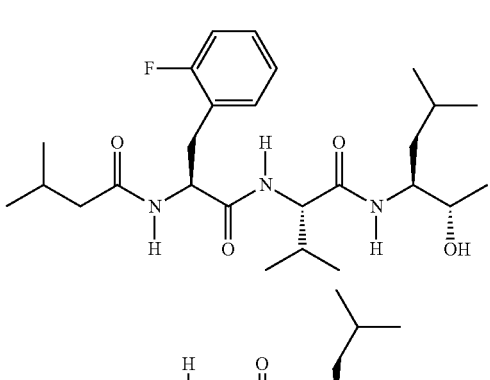 P3(o-FPhe)-pepstatin | 751.5 | ~20 nM | ~20 nM | ~50 nM | ~100 nM |

TABLE 1-continued
IC$_{50}$ values for different inhibitors on the activity of Sap1, Sap3 and Sap6 of *Candida albicans*.
| name | | MW | IC50 Sap1 | Sap3 | Sap5 | Sap6 |
|---|---|---|---|---|---|---|
| 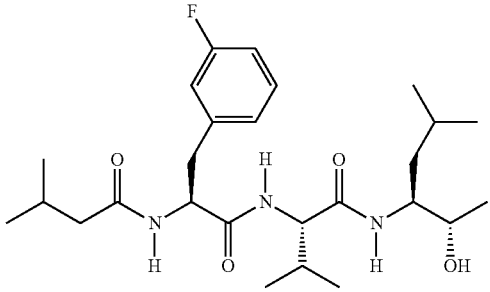 M | P3(m-FPhe)-pepstatin | 751.5 | 10 nM | ~10 nM | ~10 nM | 10 nM |
| 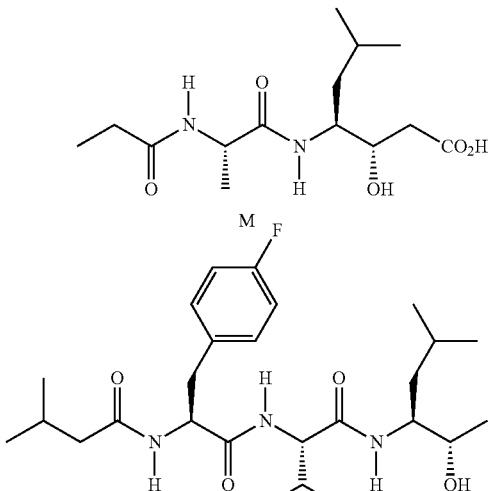 N | P3(p-FPhe)-pepstatin | 751.5 | <5 nM | <5 nM | | ~10 nM |
| 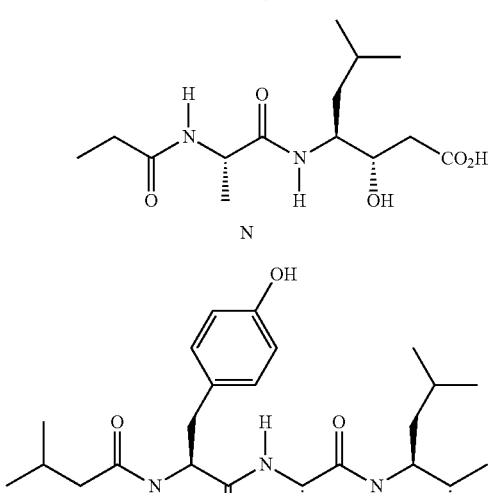 P | P3(Tyr)-pepstatin | 749.47 | <5 nM | <5 nM | | <5 nM |

TABLE 1-continued
IC$_{50}$ values for different inhibitors on the activity of Sap1, Sap3 and Sap6 of *Candida albicans*.
| name | MW | IC50 Sap1 | Sap3 | Sap5 | Sap6 |
|---|---|---|---|---|---|
| P3(MePhe)-pepstatin | 747.5 | ~10 nM | ~5 nM | | ~20 nM |
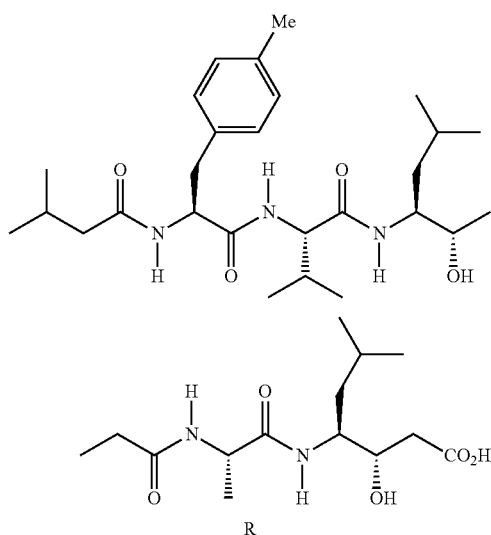
R
| | | | | | |
|---|---|---|---|---|---|
| P3(O—MeTyr)-pepstatin | 763.5 | >500 nM | ~5 nM | | ~10 nM |
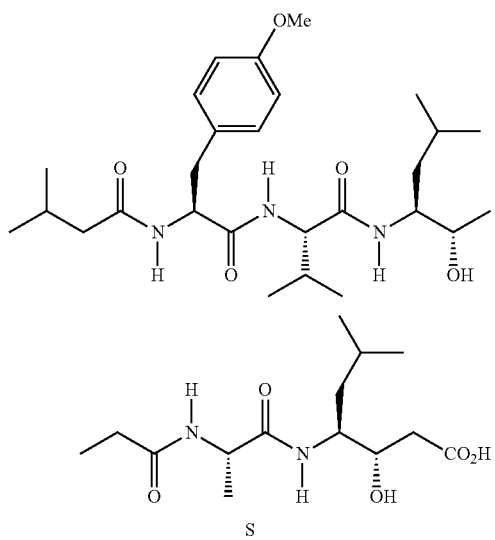
S

TABLE 1-continued

IC₅₀ values for different inhibitors on the activity of Sap1, Sap3 and Sap6 of *Candida albicans*.

| name | MW | IC50 Sap1 | Sap3 | Sap5 | Sap6 |
|---|---|---|---|---|---|
| Compound K | 918.5 | <5 nM | 20 nM | ~5 nM | ~50 nM |

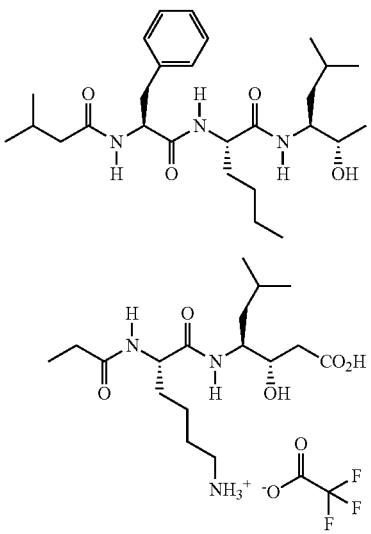

K

It can be seen from table 1 that pepstatin A derivates according to above formulae A-T show a Sap inhibition efficacy which is in most cases comparable to that of pepstatin A or even better (e.g. compounds E, J, N, P and K are more effective against Sap1 than pepstatin A itself). Additionally, compound G shows a very high specificity for Sap3 and can be thus used for selectively inhibiting Sap3 more than concomitantly inhibiting Sap1 and Sap6. Compounds H and P have increased effects on Sap 6, whereas compound K also shows an increased effect on Sap 5.

Further, pepstatin A derivatives according to above formulae A-T show unexpectedly much better overall $IC_{50}$ values as compared to structurally related known derivatives (JP 54-163826 A, WO 94/24150 A2 and WO 96/12738 A2).

Still further, pepstatin A derivates according to above formulae A-T show significantly better $IC_{50}$ values (in the range of nanomole per litre) as compared to the HIV protease inhibitors amprenavir, ritonavir and lopinavir known from prior art ($IC_{50}$ values in the range of micromole per litre). E. g., compound E is as effective as amprenavir in inhibiting Sap1 already at a concentration which is 1000-fold less than that of amprenavir.

Example 5

Comparison Between Peptide Synthesis Approaches Using Either O-Protected or Non-O-Protected Statine To show the higher yield of synthesized peptide by using O-protected statine (cf. example 1) as compared to using non-O-protected statine, according comparative examples were made.

A pentapeptide according to formula (VIII), Iva-Val-Leu-Sta-Ala-Sta, was prepared using both O-protected and non-O-protected statine approaches. In the O-protected statine approach, N-Fmoc-O-TBS statine was used. In the non-O-protected statine approach, N-Fmoc-statine was used. The syntheses were performed via Fmoc-based SPPS custom protocols using a Syro XP synthesizer. Fmoc deprotection was carried out in two steps with 40% piperidine in DMF and 20% piperidine in DMF, respectively.

In general, the amino acid coupling was effected by using a solution of Fmoc-amino acid/DIPEA in N-methylpyrrolidinone (NMP) in the presence of a DMF solution of HOBt/TBTU (HOBt stands for hydroxybenzotriazole and TBTU stands for 2-(1H-benzotriazole-1-yl)-1,1,3,3-tetramethyluronium-tetrafluoroborate).

The O-protected and non-O-protected statine were added manually. The last step, the acylation of the N-terminal group, was also performed manually as described in example 2, step 4.

After cleavage of the peptide from the resin and removal of the protecting groups (cf. example 2, step 5) the crude peptides were analyzed by analytical HPLC.

Analytical HPLC was carried out on a LaChrom-HPLC L-7000 interface (Merck) equipped with two HPLC pumps L-7100, a diode array continuous flow detector L-7450 and an autosampler L-7200 with a 100 µl sample loop. A Capell C8(2) column (5 µm particle size, 300 Å pore size, 250×4.60 mm inner diameter, Shiseido, Japan) was used. The gradient elution was performed with solutions A and B, where A was 100% $H_2O$ and 0.1% TFA (v/v), and B was 100% ACN and 0.1% TFA (v/v). The applied gradient for the analyses was a linear gradient from 100% A to 20% A and 80% B over 30 minutes.

FIG. 1 shows the chromatogram of an HPLC analysis of crude Iva-Val-Leu-Sta-Ala-Sta which was prepared via the non-O-protected statine approach. For better illustration, the percentage of B is indicated in the chromatogram, too.

Figure 2:
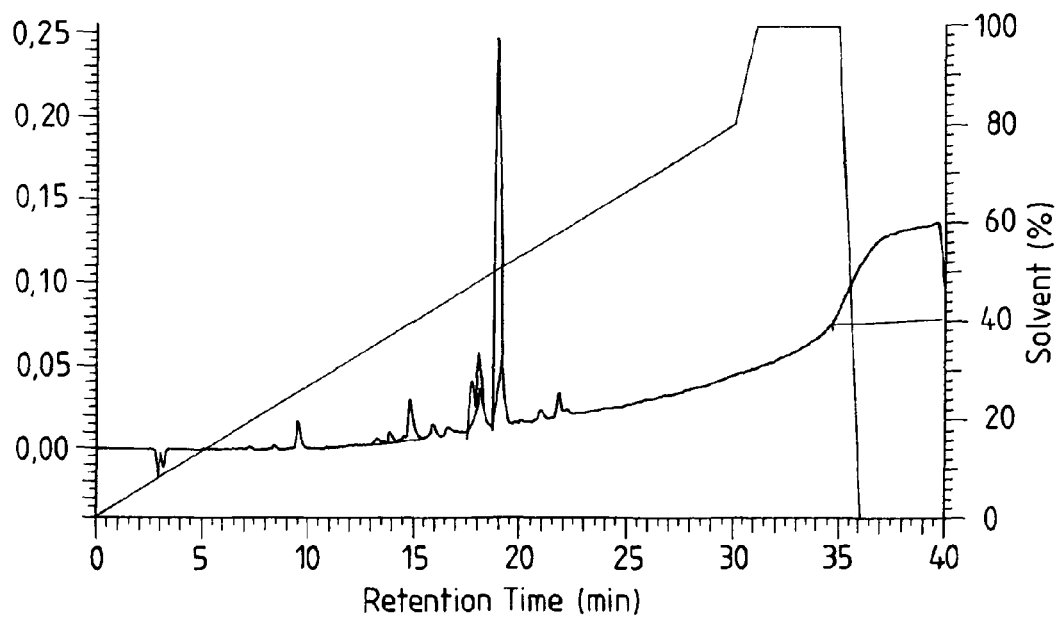

FIG. 2 shows the chromatogram of an HPLC analysis of crude Iva-Val-Leu-Sta-Ala-Sta which was prepared via the O-protected statine approach. For better illustration, the percentage of B is indicated in the chromatogram, too.

It can be seen from the chromatograms of FIGS. 1 and 2 that the non-O-protected statine approach (using statine with a free hydroxyl group) (FIG. 1) gave rise to more side products than the O-protected statine approach (FIG. 2). Purification of the crude peptides by preparative HPLC afforded the pepstatin analogues in total yields after purification of 23% for the non-O-protected statine approach, and 35% for the O-protected statine approach.

The invention claimed is:

1. A compound of the following structure:

Iva-Phe-Nle-Sta-Lys-Sta     (VI).

2. A compound selected from the group consisting of compounds having the following structure:

$R^{10}$-Val-Sta-E-Sta     (V)

wherein

E is a positively charged amino acid and $R^{10}$ is Val or N-Iva-Val.

3. The compound according to claim 2, wherein E is Lys, Orn, Dab or Arg.

4. The compound according to claim 2, wherein E is Lys, Orn or Arg.

5. The compound according to claim 2, wherein E is Lys.

6. A method of treating fungal diseases, malaria, peptic ulcer, HIV or hypertension comprising administering to a human in need thereof a compound according to claim 2.

7. A method of treating plants which are affected by a fungal disease by subjecting them to a compound according to claim 2.

8. A method for synthesizing a peptide according to claim 2, comprising the following steps:
   a) synthesizing a double protected statine by derivatizing the amino group of statine with a third protecting group and the side chain hydroxyl group of statine with a fourth protecting group,
   b) applying said double protected statine to a resin being suited for solid phase peptide synthesis,
   c) allowing formation of a plurality of bonds, each between a molecule of said double protected statine and a linker being present on the resin,
   d) capping linkers which are not bonded to a molecule of said double protected statine,
   e) cleaving the third protecting group of said double protected statine, resulting in formation of single protected statine,
   f) applying another amino acid, the a amino group of which—or if there is no a amino group, the amino group of which—is protected with the third protecting group, to the resin, and a reactive side chain of which is protected by another protecting group,
   g) allowing formation of a plurality of bonds, each between a molecule of the amino acid applied in step f) and the lastly applied amino acid,
   h) removing amino acid molecules not bonded in step g),
   i) cleaving the third protecting group of the amino acid applied in step f),
   j) repeating steps f) to i) three times and
   k) at least partially cleaving remaining protecting groups from the synthesized peptide and the synthesized peptide itself from the resin to obtain a peptide according to the general structure $R^{10}$-Val-Sta-E-Sta (V),
   wherein
   E is a positively charged amino acid and
   $R^{10}$ is Val or N-Iva-Val.

9. The method according to claim 8, wherein the fourth protecting group and the other protecting group are each different from the third protecting group.

10. The method according to claim 8, wherein the third protecting group and/or the fourth protecting group are independently selected from the group comprising tent-butyl, tert-butyloxycarbonyl, tert-butyldimethylsilyl, benzyl, benzyloxycarbonyl, 2-chloro-benzyloxycarbonyl, trityl, allyl, isovaleryl, 2,2,4,6, 7-pentamethyldihydrobenzofuran-5-sulfonyl and 9-fluorenylmethoxycarbonyl.

11. A method of treating fungal diseases, malaria, peptic ulcer, HIV or hypertension comprising administering to a human subject in need thereof a compound according to claim 1.

12. A method of treating plants which are affected by a fungal disease by subjecting them to a compound according to claim 1.

13. A method of inhibiting beta-secretase comprising administering to a human subject afflicted with Alzheimer's disease a compound according to claim 1.

14. A method of inhibiting beta-secretase comprising administering to a human subject afflicted with Alzheimer's disease a compound according to claim 2.

\* \* \* \* \*

UNITED STATES PATENT AND TRADEMARK OFFICE
CERTIFICATE OF CORRECTION

PATENT NO. : 8,809,498 B2  
APPLICATION NO. : 12/990247  
DATED : August 19, 2014  
INVENTOR(S) : Borelli et al.

Page 1 of 1

It is certified that error appears in the above-identified patent and that said Letters Patent is hereby corrected as shown below:

On the title page, item (56), References Cited under "OTHER PUBLICATIONS", in Column 2, Line 36, delete "et al," and insert -- et al., --, therefor at each occurrence throughout the Other Publications.

On title page 2, item (56), References Cited under "OTHER PUBLICATIONS", in Column 1, Line 1, delete "et al:" and insert -- et al.: --, therefor at each occurrence throughout the Other Publications.

In the Specification

In Column 2, Line 12, delete "is" and insert -- it --, therefor.

In Column 2, Line 63, delete "namley" and insert -- namely --, therefor.

In Column 7, Line 52, delete "a amino" and insert -- α amino --, therefor.

In Column 11, Line 48, delete "quartenary" and insert -- quaternary --, therefor.

In Column 15, Line 47, delete "N/e-Sta-Ala" and insert -- Nle-Sta-Ala --, therefor.

In Column 34, Lines 35-36, delete "N-methylpyrrolidinone (NMP)" and insert -- N-methylpyrrolidone (NMP) --, therefor.

In the Claims

In Column 49, Line 49, in Claim 8, delete "a amino" and insert -- α amino --, therefor.

In Column 49, Line 50, in Claim 8, delete "a amino" and insert -- α amino --, therefor.

In Column 50, Line 32, in Claim 10, delete "tent-butyl," and insert -- tert-butyl, --, therefor.

Signed and Sealed this  
Thirty-first Day of March, 2015

Michelle K. Lee  
*Director of the United States Patent and Trademark Office*

```
                          SEQUENCE LISTING

<160> NUMBER OF SEQ ID NOS: 19

<210> SEQ ID NO 1
<211> LENGTH: 6
<212> TYPE: PRT
<213> ORGANISM: Artificial
<220> FEATURE:
<223> OTHER INFORMATION: Pepstatine A Derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 1

Xaa Val Lys Xaa Ala Xaa
1               5

<210> SEQ ID NO 2
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (3)..(3)
<223> OTHER INFORMATION: Xaa at position 3 is norleucine
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 2

Xaa Val Xaa Xaa Ala Xaa
1               5

<210> SEQ ID NO 3
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (3)..(3)
<223> OTHER INFORMATION: Xaa at position 3 is DfpGly
```

```
      (Difluoropropylglycine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 3

Xaa Val Xaa Xaa Ala Xaa
1               5

<210> SEQ ID NO 4
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 4

Xaa Val Leu Xaa Ala Xaa
1               5

<210> SEQ ID NO 5
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (3)..(3)
<223> OTHER INFORMATION: Xaa at position 3 is 2-aminobutyric acid
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 5

Xaa Val Xaa Xaa Ala Xaa
1               5

<210> SEQ ID NO 6
<211> LENGTH: 6
<212> TYPE: PRT
<213> ORGANISM: Artificial
<220> FEATURE:
<223> OTHER INFORMATION: Pepstatine A derivative
<220> FEATURE:
```

```
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (3)..(3)
<223> OTHER INFORMATION: Xaa at position 3 is TfeGly
      (Trifluoroethylglycine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 6

Xaa Val Xaa Xaa Ala Xaa
1               5

<210> SEQ ID NO 7
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 7

Xaa Val Val Xaa Lys Xaa
1               5

<210> SEQ ID NO 8
<211> LENGTH: 6
<212> TYPE: PRT
<213> ORGANISM: Artificial
<220> FEATURE:
<223> OTHER INFORMATION: Pepstatine A Derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (5)..(5)
<223> OTHER INFORMATION: Xaa at position 5 is ornithine
<220> FEATURE:
<221> NAME/KEY: MISC_FEATURE
<222> LOCATION: (6)..(6)
<223> OTHER INFORMATION: Xaa at position 6 is statine

<400> SEQUENCE: 8

Xaa Val Val Xaa Xaa Xaa
1               5
```

```
<210> SEQ ID NO 9
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (5)..(5)
<223> OTHER INFORMATION: Xaa at position 5 is 2,4-diaminobutanoic acid
<220> FEATURE:
<221> NAME/KEY: MISC_FEATURE
<222> LOCATION: (6)..(6)
<223> OTHER INFORMATION: Xaa at position 6 is statine

<400> SEQUENCE: 9

Xaa Val Val Xaa Xaa Xaa
1               5

<210> SEQ ID NO 10
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 10

Xaa Val Val Xaa Arg Xaa
1               5

<210> SEQ ID NO 11
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: xaa at position 6 is statine

<400> SEQUENCE: 11
```

```
Xaa Leu Val Xaa Ala Xaa
1               5

<210> SEQ ID NO 12
<211> LENGTH: 6
<212> TYPE: PRT
<213> ORGANISM: Artificial
<220> FEATURE:
<223> OTHER INFORMATION: Pepstatine A Derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 12

Xaa Phe Val Xaa Ala Xaa
1               5

<210> SEQ ID NO 13
<211> LENGTH: 6
<212> TYPE: PRT
<213> ORGANISM: Artificial
<220> FEATURE:
<223> OTHER INFORMATION: Pepstatine A Derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (2)..(2)
<223> OTHER INFORMATION: Xaa at position 2 is oFPhe (ortho-
      Fluorophenylalanine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 13

Xaa Xaa Val Xaa Ala Xaa
1               5

<210> SEQ ID NO 14
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (2)..(2)
<223> OTHER INFORMATION: Xaa at position 2 is mFPhe (meta-
      Fluorophenylalanine)
<220> FEATURE:
<221> NAME/KEY: MISC_FEATURE
```

```
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 14

Xaa Xaa Val Xaa Ala Xaa
1               5

<210> SEQ ID NO 15
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (2)..(2)
<223> OTHER INFORMATION: Xaa at position 2 is pFPhe (para-
      Fluorophenylalanine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 15

Xaa Xaa Val Xaa Ala Xaa
1               5

<210> SEQ ID NO 16
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 16

Xaa Tyr Val Xaa Ala Xaa
1               5

<210> SEQ ID NO 17
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
```

```
<223> OTHER INFORMATION: Xaa at position 1 is isovaleryl protecting
      group
<220> FEATURE:
<221> NAME/KEY: MISC_FEATURE
<222> LOCATION: (2)..(2)
<223> OTHER INFORMATION: Xaa at position 2 is pMePhe (para-
      methylphenylalanine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 17

Xaa Xaa Val Xaa Ala Xaa
1               5

<210> SEQ ID NO 18
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (2)..(2)
<223> OTHER INFORMATION: Xaa at position 2 is O-MeTyr (O-Methyltyrosine)
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
<222> LOCATION: (6)..(6)
<223> OTHER INFORMATION: Xaa at position 6 is statine

<400> SEQUENCE: 18

Xaa Xaa Val Xaa Ala Xaa
1               5

<210> SEQ ID NO 19
<211> LENGTH: 6
<212> TYPE: PRT
<213> ORGANISM: Artificial
<220> FEATURE:
<223> OTHER INFORMATION: Pepstatine A derivative
<220> FEATURE:
<221> NAME/KEY: MISC_FEATURE
<222> LOCATION: (1)..(1)
<223> OTHER INFORMATION: Xaa at position 1 is isovaleryl protecting
      group
<220> FEATURE:
<221> NAME/KEY: MISC_FEATURE
<222> LOCATION: (3)..(3)
<223> OTHER INFORMATION: Xaa at position 3 is norleucine
<220> FEATURE:
<221> NAME/KEY: MISC_FEATURE
<222> LOCATION: (4)..(4)
<223> OTHER INFORMATION: Xaa at position 4 is statine
<220> FEATURE:
<221> NAME/KEY: MISC_FEATURE
```

```
<222> LOCATION: (6)..(6)
<223> OTHER INFORMATION: Xaa at position 6 is statine

<400> SEQUENCE: 19

Xaa Phe Xaa Xaa Lys Xaa
1               5
```